US006844038B2

(12) United States Patent
Gollier et al.

(10) Patent No.: US 6,844,038 B2
(45) Date of Patent: Jan. 18, 2005

(54) PEELABLE OVERPOUCH FILMS

(75) Inventors: Paul-Andre Gollier, Brussels (BE); Patrick Balteau, Evelette (BE); Jean-Pierre Hartman, Rhode Saint Genese (BE); Franco Peluso, Heverlee (BE)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 0 days.

(21) Appl. No.: 10/351,004

(22) Filed: Jan. 24, 2003

(65) Prior Publication Data

US 2004/0146669 A1 Jul. 29, 2004

(51) Int. Cl.[7] .................................................. B32B 7/06
(52) U.S. Cl. ...................... 428/35.7; 428/349; 428/516
(58) Field of Search ............................... 428/35.7, 349, 428/516, 476.1, 520

(56) References Cited

U.S. PATENT DOCUMENTS

| | | | |
|---|---|---|---|
| 4,540,416 A | 9/1985 | Hattori et al. | |
| 4,916,198 A | 4/1990 | Scheve et al. | |
| 5,047,475 A | 9/1991 | Ogawa et al. | |
| 5,267,646 A | 12/1993 | Inoue et al. | |
| 5,416,169 A | 5/1995 | Saito et al. | |
| 5,423,421 A | 6/1995 | Inoue et al. | |
| 5,459,978 A | 10/1995 | Weiss et al. | |
| 5,478,617 A | * 12/1995 | Watanabe et al. | 428/35.2 |
| 5,605,936 A | 2/1997 | DeNicola, Jr. et al. | |
| 5,716,698 A | * 2/1998 | Schreck et al. | 428/323 |
| 5,985,388 A | 11/1999 | Tomita et al. | |
| 6,117,505 A | 9/2000 | Weiss et al. | |
| 2002/0115795 A1 | * 8/2002 | Shang et al. | 525/192 |

FOREIGN PATENT DOCUMENTS

| | | | |
|---|---|---|---|
| EP | 0240563 | * | 5/1990 |
| JP | 08295003 A | * | 11/1996 |
| JP | 0924888 A | * | 9/1997 |

* cited by examiner

*Primary Examiner*—Sandra M. Nolan
(74) *Attorney, Agent, or Firm*—Jane J. Choi; Paula J. F. Kelly; Bell, Boyd & Lloyd

(57) ABSTRACT

The present invention provides a peelable polymeric layer structure having a first sealant layer including an ethylene-containing polymer, and a second sealant layer including a polypropylene-containing polymer attached to the first sealant layer along a peelable seal. The present invention also provides an overpouch container including a first sidewall having a first sealant layer of an ethylene-containing polymer, and a second sidewall having a second sealant layer of a propylene containing polymer. The second sealant layer is attached to the first sealant layer along a peelable peripheral seal.

66 Claims, 4 Drawing Sheets

FIG.2a
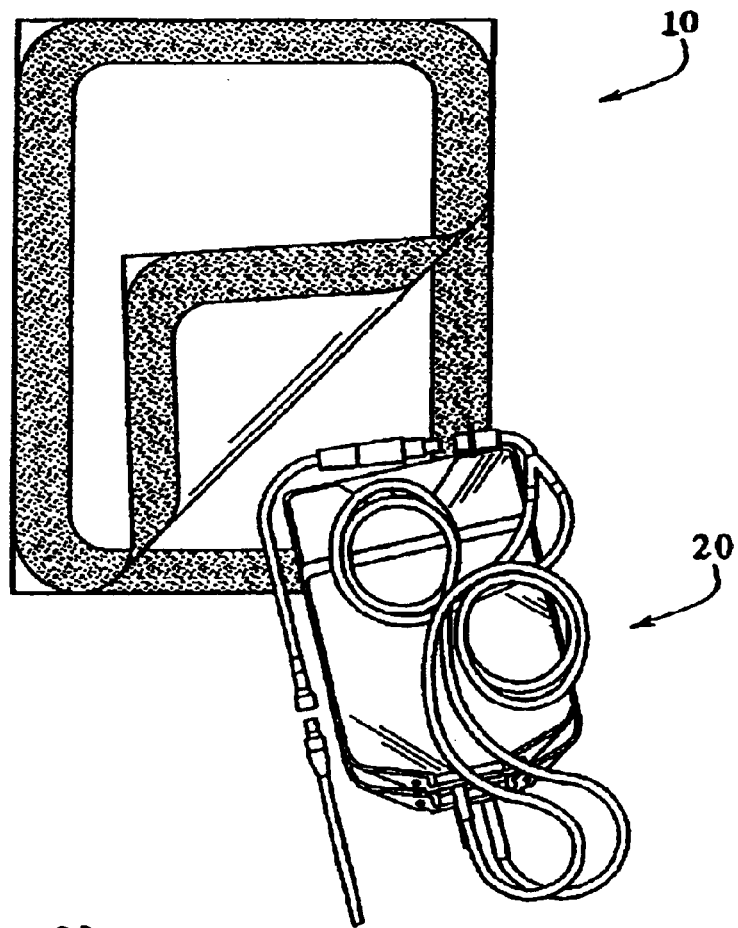
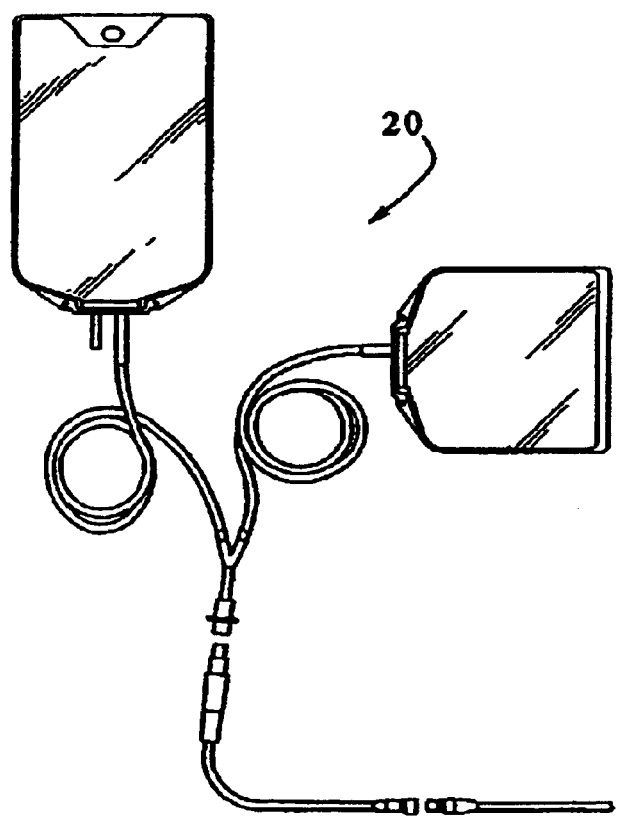
FIG.2b

PEELABLE OVERPOUCH FILMS

BACKGROUND OF THE INVENTION

1. Technical Field

The present invention relates generally to polymeric layer structures that feature a peelable seal and more specifically to the use of such materials for the manufacture of a peelable overpouch and the like.

2. Background of the Invention

In the medical field, primary containers are used to collect, store, transport, and ultimately deliver therapeutic fluids, nutritional solutions, respiratory therapy agents, dialysis solutions, blood, blood products, plasma derivatives, plasma expanders, blood substitutes, anti-coagulants, blood preservatives, and other therapeutic agents. Oftentimes, these primary containers are placed into secondary containers such as an overpouch to maintain the integrity and volume of the agent contained within the primary container. The primary container can be attached to a tubing set or tubing sets and be accompanied by other containers to form a therapeutic fluid delivery set. The overpouch must have a unique combination of properties. For example, it is desirable that the overpouch be optically transparent in order to inspect visually the contents of the primary container for contaminants to the agent contained therein. At a minimum, the transparency must permit the container's label copy to be legible. The material must also be functional over a wide range of temperatures, including the ability to withstand the autoclaving or sterilization process, which is usually accomplished using steam at temperatures of about 121° C. and at elevated pressures.

The overpouch must also be compatible with the film that constitutes the primary container and with itself. That is, the overpouch cannot become wrinkled, discolored, or adhered to other overpouches or to the primary container, each of which would impair (if not preclude) the ability to inspect visually the primary container without removing the overpouch.

The overpouch must also allow easy access to the inside, primary container by providing an "easy-open" feature such as a tear strip, notch, slit, or the like where no cutting implement is needed.

It is also desirable that the overpouch be free from, or have a low content of, low molecular weight additives such as plasticizers, stabilizers and the like, which could be released into the medications or biological fluids that are contained within the primary container inside the overpouch, thereby potentially causing danger to patients who are using such devices. Hitherto, the industry standard material for fabricating an overpouch has been a high density polyethylene (HDPE), such as Fina 7194, which is sold commercially by AtoFina Oil and Chemical Co.

The present invention is provided to solve these and other problems.

SUMMARY OF THE INVENTION

The present invention provides a peelable polymeric layer structure having a first sealant layer including an ethylene-containing polymer, and a second sealant layer including a polypropylene-containing polymer attached to the first sealant layer along a peelable seal.

The present invention also provides an overpouch container including a first sidewall having a first sealant layer of an ethylene-containing polymer, and a second sidewall having a second sealant layer of a propylene containing polymer. The second sealant layer is attached to the first sealant layer along a peelable peripheral seal. These and other aspects and attributes of the present invention will be discussed with reference to the following drawings and accompanying specification.

BRIEF DESCRIPTION OF THE DRAWINGS

FIG. 2a is a perspective view of a peelable seal overpouch of the present invention, the overpouch partially containing a peritoneal dialysis set.

FIG. 2b is a perspective view of a peritoneal dialysis delivery system.

DETAILED DESCRIPTION OF THE PREFERRED EMBODIMENT

Figure 1:
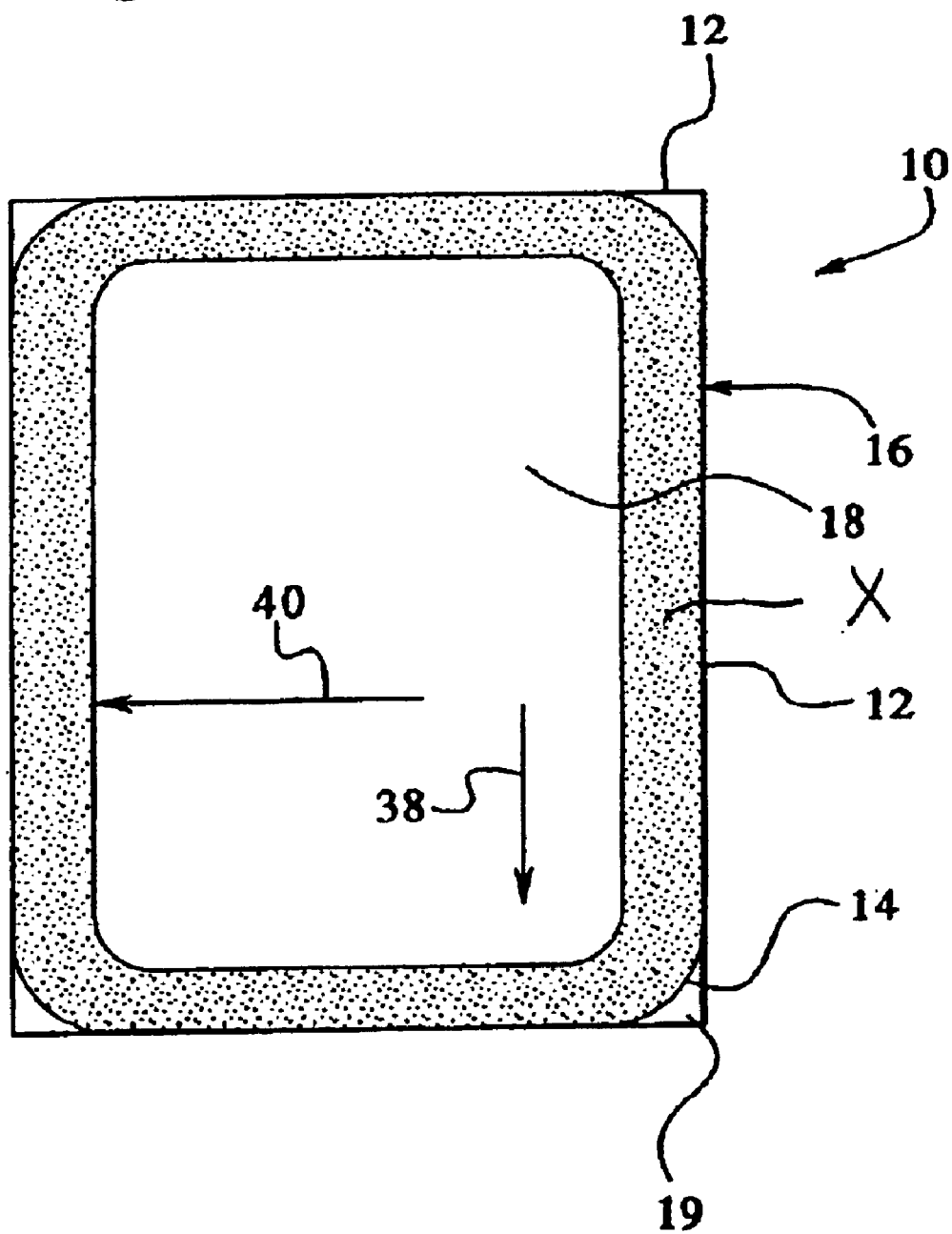
FIG. 1 is a perspective view of a peelable seal overpouch of the present invention.

While this invention is susceptible of embodiment in many different forms, there is shown in the drawing, and will be described herein in detail, specific embodiments thereof with the understanding that the present disclosure is to be considered as an exemplification of the principles of the invention and is not intended to limit the invention to the specific embodiments illustrated.

According to the present invention, polymeric layer structures and peelable overpouches made from same are provided which meet the requirements set forth above. The peelable overpouch provides easy access to the contents by proving a peel seal formed by sealing a peripheral portion of the sidewalls of the overpouch together. The peel seal should be strong enough to remain intact and air-tight throughout typical transport and storage processes until the time at which the packaging is opened by the end user. The peel seal should not be so permanent that it cannot be easily unsealed (i.e., peeled open) by the end user by pulling the films apart using normal hand pressure.

It is also important that this balance of seal strength and ease of peelability remain relatively constant from initial construction of the sealed package until the package is intended to be opened. This is a special concern when the package is intended to be subjected to extreme temperature fluctuations prior to opening. For example, sealed packages containing food products are often designed to be stored under freezing conditions and ultimately placed into a heat source such as a microwave oven or a container of boiling water.

It is well-known that various medical supplies require sterilization prior to use. A common heat-sterilization technique involves the use of an autoclave process to destroy microorganisms. A polymeric film packaging system with a durable yet peelable seal can be used to enclose medical supplies that require sterilization prior to use. In this regard, the peelable seal must withstand the high temperatures associated with sterilization and maintain its peelability thereafter.

FIG. 1 shows a peelable overpouch 10 having opposed first and second sidewalls 12, 14 sealed together along a peripheral portion to form a peel seal 16. The sidewalls can be of a multiple layer structure or a monolayer structure. One sidewall can be a multiple layer structure while the opposite sidewall is of a monolayer structure. The width of the seal can be sufficiently narrow, defining a chamber 18 wherein contents can be placed prior to complete sealing of the overpouch. At one or more locations outside the perimeter of the seal, a portion of the unsealed webs remain as tab-like grip zones 19 that can be grasped with the fingers or otherwise to initiate the pulling process necessary to unseal the seal.

FIG. 2a shows a peelable overpouch 10 in accordance with the present invention partially containing a continuous ambulatory peritoneal dialysis set 20. This set 20 is shown unpacked in FIG. 2b. It is contemplated enclosing various therapeutic solution containers such as I.V. solutions, drug solutions, blood, blood products, renal solutions, plasma derivatives, plasma expanders, blood substitutes, anti-coagulants, blood preservatives, and other therapeutic agents. It is also contemplated storing other medical devices such as surgical equipment, administration sets, solution containers, and the like. However, it must be understood that articles for packaging with the peelable overpouch are not limited to medical devices, and, therefore, the nature and type of such articles will vary greatly depending on the desired application.

Figure 3:
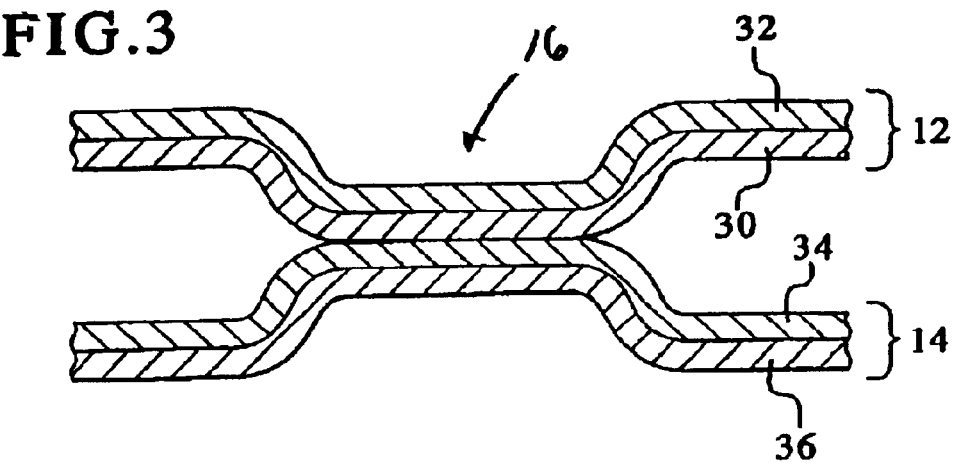
FIG. 3 is a schematic view of a polymeric layer structure of the present invention.
Figure 4:
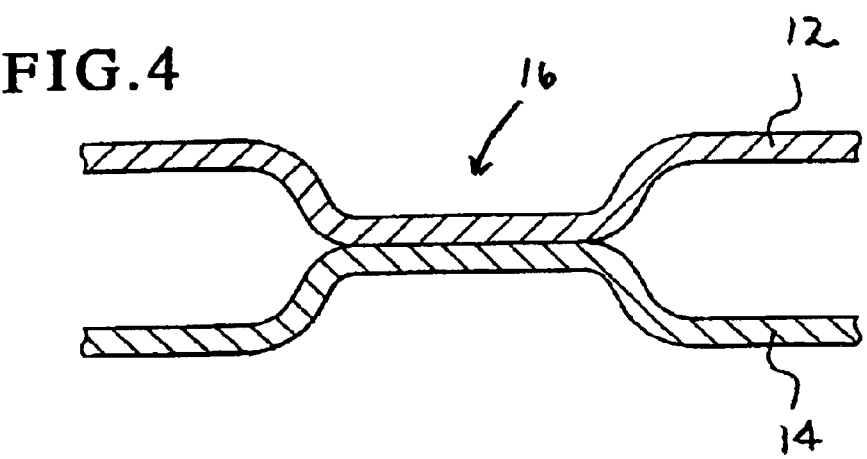
FIG. 4 is a schematic view of a further polymeric layer structure of the present invention.

FIG. 3 shows, in a preferred form of the invention, the first sidewall 12 and the second sidewall 14 are both multilayer structures and FIG. 4 shows the first sidewall 12 and the second sidewall 14 are both monolayer structures. FIG. 3 shows the first sidewall 12 has a first sealant layer 30 and first external layer 32. The second sidewall 14 has a second sealant layer 34 and a second external layer 36. All or part of the first and second sidewalls can be sealed together, the seal being formed between the inner sealant surfaces of the respective sidewalls. It is contemplated one sidewall can be of a multilayer structure and the opposite sidewall can be a monolayer or multiple layer structure having the same or different number of layers from the other sidewall.

The peel seal 16 can be pulled apart by initiating the unsealing process at designated grip zones 19. As the two sidewalls are progressively peeled apart, the contents therein correspondingly become progressively exposed. Continued peeling can ultimately result in complete separation of the two sidewalls 12 and 14. The seal 16 is designed to be pulled apart in any direction that runs substantially parallel along the length of the seal. Therefore, seal separation at a location X in FIG. 1 is facilitated by pulling the sidewalls in a direction 38 at right angles with the width of the seal 16, whereas the seal is relatively resistant to separation when pulling the sidewalls in the direction 40 parallel to the width of the seal 16.

The seal between the sidewalls is ideally achieved by sealing at a temperature higher than the melting point of the inner sealant layers 30 and 34. At least one of the external layers 32 or 36 should have a melting point temperature above the sealing temperature to avoid compromising the integrity of the external surface that is contacted by the sealing die.

The adhesion or peel strength between sealed portions of the sidewalls is controlled by at least two different phenomena. First, without being bound to a particular theory, it is believed that the first phenomenon is mechanical interlocking produced by viscous flow generated between the two sealant layers as they are melted by the die. As noted above, this produces a high peel strength when peeled in a direction perpendicular to the seal direction. Additionally, the seal is more easily peelable in the direction parallel to the seal, an attribute that is believed to be controlled largely by the pressure applied to the sealing die.

A second phenomenon contributing to the seal properties of the present invention relates to the composition of the materials selected for the sealant layers. It is known that non-permanent seals can be formed by combining incompatible materials. More specifically, materials with high compatibility tend to form stronger seals, while materials of low compatibility form weaker seals.

Suitable materials for the first sealant layer 30 are selected from polyolefins derived from α-olefin monomers having from 2 to 20 carbons. Accordingly, suitable polyolefins include homopolymers, copolymers and terpolymers of ethylene, propylene, butene, pentene, hexene, heptene, octene, etc and blends composed thereof.

In one preferred form of the invention, the polyolefin is an ethylene homopolymer or copolymer. Ethylene homopolymers include high density polyethylene (HDPE), medium density polyethylene (MDPE) and low density polyethylene (LDPE) and most preferably is HDPE. Suitable HDPEs include those having a density greater than 0.915 g/cc to about 0.970 g/cc, and even more preferably from about 0.955 g/cc to about 0.965 g/cc.

Suitable copolymers of ethylene are obtained by polymerizing ethylene monomers with an α-olefin having from 3 to 20 carbons, more preferably 3–10 carbons and most preferably from 4 to 8 carbons. It is also desirable for the copolymers of ethylene to have a density as measured by ASTM D-792 of less than about 0.915 g/cc and more preferably less than about 0.910 g/cc and even more preferably less than about 0.900 g/cc. Such polymers are oftentimes referred to as VLDPE (very low density polyethylene) or ULDPE (ultra low density polyethylene). Preferably the ethylene α-olefin copolymers are produced using a single site catalyst and even more preferably a metallocene catalyst systems. Single site catalysts are believed to have a single, sterically and electronically equivalent catalyst position as opposed to the Ziegler-Natta type catalysts which are known to have a mixture of catalysts sites. Such single-site catalyzed ethylene α-olefins are sold by Dow under the trade name AFFINITY, DuPont Dow under the trademark ENGAGE®, and by Exxon under the trade name EXACT. These copolymers shall sometimes be referred to herein as m-ULDPE.

Suitable copolymers of ethylene also include ethylene and lower alkyl acrylate copolymers, ethylene and lower alkyl substituted alkyl acrylate copolymers and ethylene vinyl acetate copolymers having a vinyl acetate content of from about 8% to about 40% by weight of the copolymer. The term "lower alkyl acrylates" refers to comonomers having the formula set forth in Diagram 1:

Diagram 1

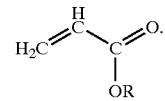

The R group refers to alkyls having from 1 to 17 carbons. Thus, the term "lower alkyl acrylates" includes but is not limited to methyl acrylate, ethyl acrylate, butyl acrylate and the like.

The term "alkyl substituted alkyl acrylates" refers to comonomers having the formula set forth in Diagram 2:

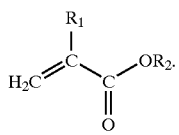

Diagram 2

$R_1$ and $R_2$ are alkyls having 1–17 carbons and can have the same number of carbons or have a different number of carbons. Thus, the term "alkyl substituted alkyl acrylates" includes but is not limited to methyl methacrylate, ethyl methacrylate, methyl ethacrylate, ethyl ethacrylate, butyl methacrylate, butyl ethacrylate and the like.

Suitable propylene containing polymers include both homopolymers and copolymers of polypropylene. Suitable homopolymers of polypropylene can have a stereochemistry of amorphous, isotactic, syndiotactic, atactic, hemiisotactic or stereoblock. In one preferred form of the invention the homopolymer of polypropylene is obtained using a single site catalyst.

Suitable copolymers of propylene are obtained by polymerizing a propylene monomer with an α-olefin having from 2 to 20 carbons. In a more preferred form of the invention the propylene is copolymerized with ethylene in an amount by weight from about 1% to about 20%, more preferably from about 1% to about 10% and most preferably from 2% to about 5% by weight of the copolymer. Propylene and ethylene copolymers with greater than 5% by weight of ethylene shall be referred to herein as propylene and ethylene copolymer with high ethylene content. The propylene and ethylene copolymers may be random or block copolymers. The propylene random copolymer can be heterophasic. What is meant by heterophasic is the production of the propylene copolymer is carried out in a two-stage process, resulting in a multiphase structure with a homopolymer matrix and inclusions consisting of amorphous EP-copolymer ("rubber") and crystalline PE. Variations of molar mass and composition of the elastomeric phase in relation to the matrix allow a wide variation of properties (stiffness, toughness and transparency).

In a preferred form of the invention, the propylene copolymer is obtained using a single-site catalyst.

It is also possible to use a blend of polypropylene and α-olefin copolymers wherein the propylene copolymers can vary by the number of carbons in the α-olefin. For example, the present invention contemplates blends of propylene and α-olefin copolymers wherein one copolymer has a 2 carbon α-olefin and another copolymer has a 4 carbon α-olefin. It is also possible to use any combination of α-olefins from 2 to 20 carbons and more preferably from 2 to 8 carbons. Accordingly, the present invention contemplates blends of propylene and α-olefin copolymers wherein a first and second α-olefin has the following combination of carbon numbers: 2 and 6, 2 and 8, 4 and 6, 4 and 8. It is also contemplated using more than 2 polypropylene and α-olefin copolymers in the blend. Suitable polymers can be obtained using a catalloy procedure.

It may also be desirable to use a high melt strength polypropylene. High melt strength polypropylenes can be a homopolymer or copolymer of polypropylene. High melt strength polypropylenes are known to have free-end long chain branches of propylene units. Methods of preparing polypropylenes which exhibit a high melt strength characteristic have been described in U.S. Pat. Nos. 4,916,198; 5,047,485; and 5,605,936 which are incorporated herein by reference and made a part hereof. One such method includes irradiating a linear propylene polymer in an environment in which the active oxygen concentration is about 15% by volume with high energy ionization energy radiation at a dose of 1 to $10^4$ megarads per minute for a period of time sufficient for a substantial amount of chain scission of the linear propylene polymer to occur but insufficient to cause the material to become gelatinous. The irradiation results in chain scission. The subsequent recombination of chain fragments results in the formation of new chains, as well as joining chain fragments to chains to form branches. This further results in the desired free-end long chain branched, high molecular weight, non-linear, propylene polymer material. Radiation is maintained until a significant amount of long chain branches form. The material is then treated to deactivate substantially all the free radicals present in the irradiated material.

High melt strength polypropylenes can also be obtained as described in U.S. Pat. No. 5,416,169, which is incorporated in its entirety herein by reference and made a part hereof, when a specified organic peroxide (di-2-ethylhexyl peroxydicarbonate) is reacted with a polypropylene under specified conditions, followed by melt-kneading. Such polypropylenes are linear, crystalline polypropylenes having a branching coefficient of substantially 1, and, therefore, has no free end long-chain branching and will have a intrinsic viscosity of from about 2.5 dl/g to 10 dl/g.

Suitable materials for the second sealant layer 34 are selected from the same group of polymeric materials as the first sealant layer 30, but is different from, and, in a preferred form of the invention, is sealing incompatible therewith. Materials are incompatible when they are non-miscible or non-mixable with each other. For example, if the first sealant layer 30 is polyethylene, the second sealant layer 34 can be polypropylene, polybutene, styrene-ethylene-butadiene-styrene (SEBS), styrene-butadiene-stryene (SBS), styrene-isoprene-styrene (SIS), or any other hydrophobic polymer.

As noted above, the inventors herein have found that various combinations of incompatible polyolefins provide suitable starting materials for the sealant layers of the present invention. The following materials are listed in order of highest to lowest compatibility with high density polyethylene: high density polyethylene, linear low density polyethylene, low density polyethylene, polypropylene random heterophasic copolymer with high ethylene content, polypropylene random copolymer with high ethylene content, and polypropylene homopolymer. In other words, in the case of these polyolefins, the highest intrinsic adhesion strength would be exhibited by a seal between high density polyethylene and high density polyethylene. Conversely, lowest adhesion would be obtained with high density polyethylene and polypropylene homopolymer.

The present invention further contemplates using polymeric blends having two or more components for the first and second sealant layers 30 and 34. In a preferred form of the invention, the polymeric blend for the first sealant layer 30 is a two-component blend having from about 95% to about 5% of a first polyolefin blended with a second polyolefin in an amount from about 5% to about 95%. The second sealant layer 34 can be a blend of two or more different polypropylene polymers described above such as a two-component blend of from about 99% to about 1% of one polypropylene and from about 1% to about 99% of a second polypropylene.

Suitable layer structures of the peel seal defined by the interfacing first sealant layer 30 second sealant layer 34 include, but are not limited to: (1) HDPE/polypropylene random copolymer (ethylene content 1–3%), and (2) HDPE/ 90% PP random copolymer with 10% PP random heterophasic copolymer. The relative amounts of the components of the blend are stated as a weight percentage unless otherwise provided.

Additional suitable layers include a first sealant layer 30 of LLDPE or MDPE, and a second sealant layer 34 of a polypropylene containing polymer. The HDPE may be Stamylex 90-89, manufactured by DEXPlastomers o.f.v. of Heerlen, The Netherlands. The MDPE may be Stamylex 40-46-48, manufactured by DEX. The LLDPE could be Stamylex 1026, also manufactured by DEX. The polypropylene containing polymer may be Borealis RD204CF, manufactured by Borealis GMBH of Burghausen, Germany, or Adflex C200F, manufactured by Basell Polyolefins Company N.V. of Hoofddorp, The Netherlands.

Other layer structures having incompatible interfacing layers include, for example, a layer of polybutene attached to a layer of polypropylene as well as a layer of polybutene attached to a layer of polyethylene.

Suitable materials for the first external layer 32 and/or second external layer 36 include homopolymers and copolymers of polyolefins, polyamides, polyesters, ethylene copolymerized with one or more monomers such as carboxylic acids having from 2 to 20 carbons and ester derivatives thereof, acrylic acid, ester derivatives or acrylic acids, alkyl substituted acrylic acid, alkyl substitutes esters of acrylic acid, vinyl acetate, vinyl acrylate and the like. In a preferred form of the invention the first external layer 32 is a polyamide, and more preferably nylon 6. Suitable nylon 6 is sold by EMS-Chemie A.G. of Domat/Ems, Switzerland under the trade name Grillon XE 3615. The external layers 32 and 36 can also include blends of such materials. In another preferred embodiment, the first external layer 32 is a polyamide, and more preferably nylon 6, and the second external layer 36 is LLDPE.

Polyamides are especially preferable as components in any external layers of the present invention. Preferably, the polyamides will be chosen from polyamides produced in a ring-opening reaction of lactams having from 4–12 carbons, aliphatic polyamides resulting from the condensation reaction of di-amines having a carbon number within a range of 2–13, aliphatic polyamides resulting from a condensation reaction of di-acids having a carbon number within a range of 2–13, polyamides resulting from the condensation reaction of dimer fatty acids, and amide-containing copolymers (random, block or graft).

Suitable polyesters include polycondensation products of di-or polycarboxylic acids and di or poly hydroxy alcohols or alkylene oxides. In a preferred form of the invention, the polyester is a polyester ether. Suitable polyester ethers are obtained from reacting 1,4 cyclohexane dimethanol, 1,4 cyclohexane dicarboxylic acid and polytetramethylene glycol ether and shall be referred to generally as PCCE. Suitable PCCE's are sold by Eastman under the trade name ECDEL. Suitable polyesters further include polyester elastomers which are block copolymers of a hard crystalline segment of polybutylene terephthalate and a second segment of a soft (amorphous) polyether glycols. Such polyester elastomers are sold by Du Pont Chemical Company under the trade name HYTREL.®.

Figure 5:
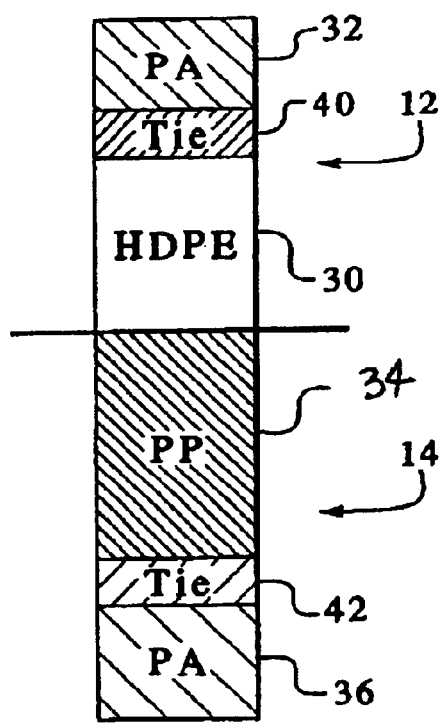
FIG. 5 is a cross-sectional view of a multilayer structure of an embodiment of the present invention.

FIG. 5 shows a preferred example of a peel seal structure having the first sidewall 12 of a multiple layer structure having a first sealant layer 30 of HDPE, a second external layer 32 of a polyamide, nylon 6, and a first tie layer 40 of maleic anhydride grafted polyethylene (MAH-PE), such as OREVAC 18305, manufactured by ATO Fina therebetween. The second sidewall 14 has a second sealant layer 34 of a PP random copolymer, a second external layer 36 of a polyamide, nylon 6, and a second tie layer 42 of maleic anhydride grafted polypropylene (MAH-PP), such as Admer QF 300 E from Mitsui Chemicals, Inc. of Tokyo, Japan therebetween. The first sidewall 12 and second sidewall 14 may sometimes also be referred to as webs.

Figure 6:
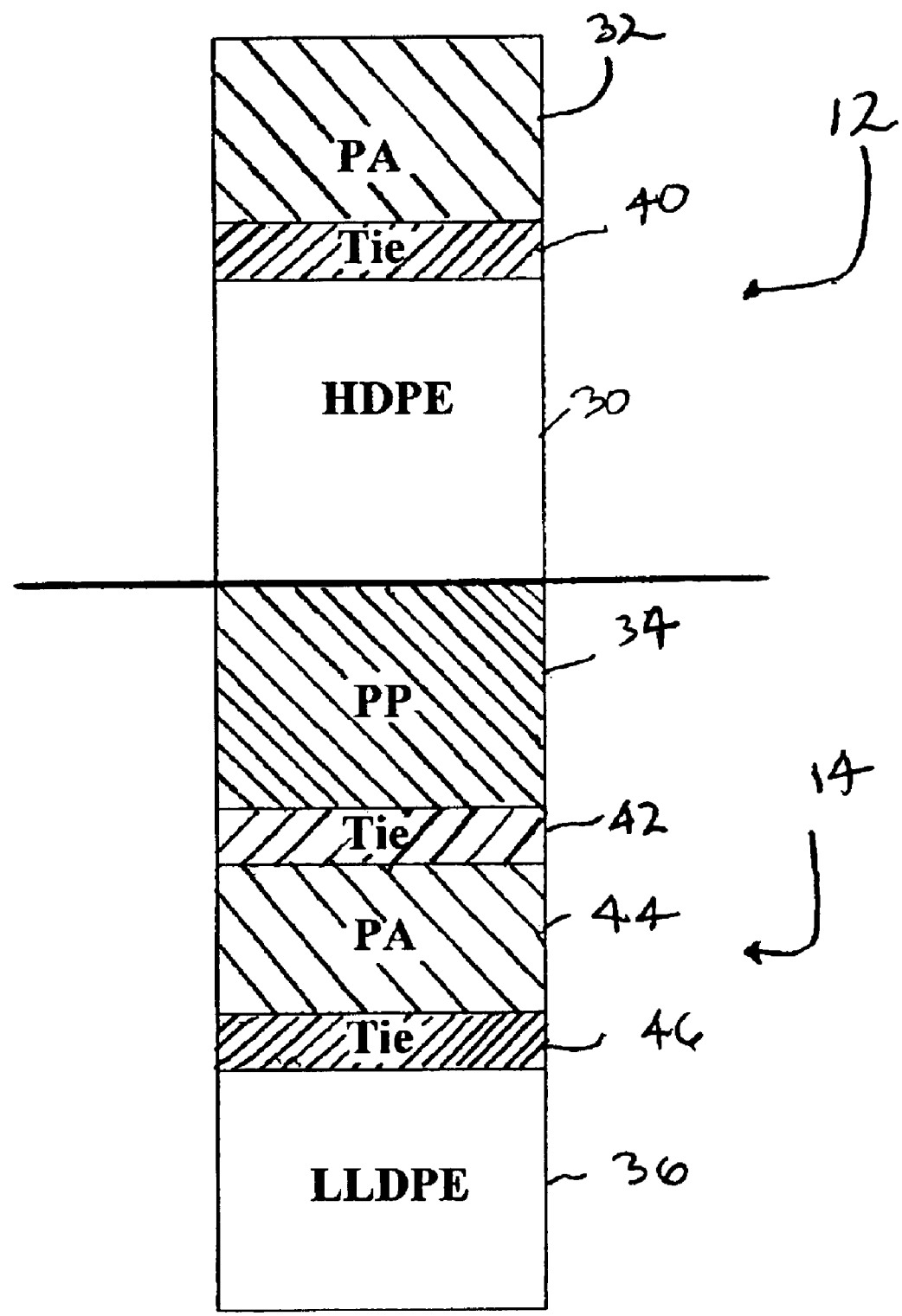
FIG. 6 is a cross-sectional view of a multilayer structure of an embodiment of the present invention.

FIG. 6 shows another preferred embodiment of the present invention having the first sidewall 12 of a multiple layer structure having a first sealant layer 30 of HDPE, a second external layer 32 of a polyamide, nylon 6, and a first tie layer 40 of maleic anhydride grafted polyethylene (MAH-PE), such as OREVAC 18305, manufactured by ATO Fina. therebetween. The second sidewall 14 has a second sealant layer 34 of a PP random copolymer, an intermediate layer 44 of a polyamide, nylon 6, and a second tie layer 42 of maleic anhydride grafted polypropylene (MAH-PP), such as Admer QF 300 E from Mitsui Chemicals, Inc. of Tokyo, Japan therebetween. In addition, the second sidewall 14 includes a third tie layer 46 and a second external layer 36. The third tie layer 42 is MAH-PP, and the second external layer 36 is LLDPE.

The tie layers may be selected from those materials known in the art. For example, suitable tie layers include modified polyolefins blended with unmodified polyolefins. The modified polyolefins are typically polyethylene or polyethylene copolymers. The polyethylenes can be ULDPE, low density (LDPE), linear low density (LLDPE), medium density polyethylene (MDPE), and high density polyethylenes (HDPE). The modified polyethylenes may have a density from 0.850–0.95 g/cc. More specifically, and by way of further example, besides MAH-PE or MAH-PP mentioned above, the tie layers can consist of modified ethylene and propylene copolymers such as those sold under the product designations PLEXAR (Quantum Chemical Co.) and BYNEL (Dupont).

The relative thicknesses of the layers of the present invention are as follows: the first external layer should have a thickness from about 5–70 microns, more preferably from 15–60 microns, or any range or combination of ranges therein. The first sealant layer should have a thickness from about 50–110 microns, more preferably from about 60–90 microns, or any range or combination of ranges therein. The second sealant layer should have a thickness from about 30–80 microns, more preferably from about 35–75 microns, or any range or combination of ranges therein. The second external layer should have a thickness from about 5–110 microns, more preferably from 15–100 microns, or any range or combination of ranges therein. The tie layers should have a thickness from about 2–12 microns, more preferably from 4–10 microns, or any range or combination of ranges therein.

Because the total number of layers of the present invention can vary depending on the intended use of the layer structure, the overall thickness of the layer structure will thus vary as well.

The seal of the present invention preferably has a strength of about 2N/15 mm to about 25N/15 mm when pulling forces are applied to the seal in a direction perpendicular to the direction of the seal. Additionally, the seal preferably has a strength of about 0.5N to about 7.6N when pulling forces are applied to the seal in a direction parallel to the direction of the seal. The seal strength will not vary by more than approximately 50% when comparing an overpouch prior to autoclave and after an autoclave procedure at 121° C. for one hour.

The sidewalls may be processed by standard techniques well known to those of ordinary skill in the art and including extrusion, coextrusion, cast coextrusion, extrusion coating, lamination or other acceptable process.

Preferably, the sidewalls are fabricated using a cast coextrusion process. The process should be essentially free of slip agents and other low molecular weight additives that may increase the extractables to an unacceptable level.

Example films having the following components and weight percentages were tested.

EXAMPLE 1

A first sheet having a first sealant layer of HDPE of 70 microns thickness, a tie layer of MAH-PE of 7 microns thickness, and a first external layer of nylon 6, 18 microns thick. It also included a second sheet having a second sealant layer of polypropylene 45 microns thick, a 9 micron thick second tie layer of MAH-PP, and an intermediate layer of nylon 6, 28 microns thick. Additionally, the second sheet included a 9 micron thick third tie layer of MAH-PP, and a second external layer of LLDPE, 90 microns thick. The first sheet was heat sealed together with the HDPE layer contacting the polypropylene layer. Example 1 corresponds to FIG. 6.

EXAMPLE 2

A first sheet having a first sealant layer of HDPE 70 microns thick, a 7 micron tie layer of MAH-PE, and a first external layer of nylon 6, 18 microns thick. It also included a second sheet having a 92 micron thick second sealant layer of 90% PP random copolymer+10% PP random heterophasic copolymer, a 9 micron thick tie layer of MAH-PP, and a second external layer of nylon 6, 56 microns thick. Example 2 corresponds to FIG. 5.

The following tests were performed on Examples 1 and 2. For both Examples, the first sheet was heat sealed to the second sheet with the HDPE layer contacting the polypropylene blend layer.

(1) Autoclavability

Autoclavability was demonstrated by making several primary bags, filling them with distilled water, overpouching them with the combination of films as defined in Example 2 above, and steam sterilizing them in an autoclave for 60 minutes at 121° C. with a 28 pounds per square inch counterpressure. The bags were then removed from the peelable overpouch by cutting open one end to keep the remainder of the overpouch for seal strength testing as described below.

(2) Mechanical Modulus and Recovery

The autoclaved film sample with a known geometry is mounted on a servohydraulically driven mechanical tester having cross heads to elongate the sample. At 10 inches (25 cm) per minute crosshead speed, the sample is elongated to about 20% elongation. At this point, the cross-heads travel and then reverse to travel in a direction opposite that originally used to stretch the sample. The stress strain behavior is recorded on a digital recorder. The elastic modulus ("E(kg/mm$^2$)") is taken from the initial slope on the stress-strain curve, and the recovery taken from the excess sample dimension as a percentage of sample elongation.

For Examples 1 and 2, the elastic modulus of the first sheet in the mach direction was 95 kg/mm$^2$, and in the cross extrusion direction was 100 kg/mm$^2$. For Example 1, the elastic modulus of the second sheet in both the mach and cross extrusion directions was 55 kg/mm$^2$. For Example 2, the elastic modulus of the second sheet in the mach direction was 90 kg/mm$^2$, and in the cross extrusion direction was 85 kg/mm$^2$.

(3) Optical Clarity

Post-autoclaved film samples are first cut into about 2 by 2 inch (5 by 5 cm) squares, mounted on a Hunber Colorimeter and their internal haze measured according to ASTM D-1003. For Examples 1 and 2, the haze % of the first sheet was 26% ±5%. For Example 1, the haze % of the second sheet was 30%±3%. For Example 2, the haze % of the second sheet was 12%±3%.

(4) Seal Strength

To determine peal seal strength, 15 mm wide strips of sealed layers were tensile tested in directions both perpendicular to and parallel to the seal direction. For Examples 1 and 2, it was found that in the direction parallel to the direction of the seal, the force required to separate the seal after steam sterilization at 121° C. was 0.50 to 7.6N/15 mm. In the direction perpendicular to the seal direction, the force required to separate the seal was 17N/15 mm.

It is understood that, given the above description of the embodiments of the invention, various modifications may be made by one skilled in the art. Such modifications are intended to be encompassed by the claims below.

What is claimed is:

1. A peelable polymeric layer structure comprising:
   a first sealant layer composed solely of an ethylene homopolymer; and
   a second sealant layer comprising a polypropylene-containing polymer attached to the first sealant layer along a peelable seal.

2. The polymeric layer structure of claim 1, wherein the ethylene homopolymer is selected from the group consisting of high density polyethylene, medium density polyethylene and linear low density polyethylene.

3. The polymeric layer structure of claim 2, wherein the first sealant layer is high density polyethylene.

4. The polymeric layer structure of claim 1, wherein the second sealant layer is selected from the group consisting of: propylene homopolymers and propylene copolymers.

5. The polymeric layer structure of claim 4, wherein the second sealant layer is a propylene homopolymer.

6. The polymeric layer structure of claim 5, wherein the propylene homopolymer has a stereochemistry selected from the group of: (a) amorphous, (b) isotactic, (c) syndiotactic, (d) atactic, (e) hemiisotactic, and (f) stereoblock.

7. The polymeric layer structure of claim 5, wherein the propylene homopolymer is obtained using a single site catalyst.

8. The polymeric layer structure of claim 4, wherein the second sealant layer is a propylene copolymer.

9. The polymeric layer structure of claim 8, wherein the propylene copolymer is obtained by polymerizing a propylene monomer with an α-olefin having from 2 to 20 carbons.

10. The polymeric layer structure of claim 8, wherein propylene is copolymerized with ethylene in an amount by weight from about 1% to about 20% of the copolymer.

11. The polymeric layer structure of claim 10, wherein propylene is copolymerized with ethylene in an amount by weight from about 1% to about 10% of the copolymer.

12. The polymeric layer structure of claim 10, wherein propylene is copolymerized with ethylene in an amount by weight from about 2% to about 5% of the copolymer.

13. The polymeric layer structure of claim 10, wherein the propylene and ethylene copolymer is a random copolymer.

14. The polymeric layer structure of claim 10, wherein the propylene and ethylene copolymer is a block copolymer.

15. The polymeric layer structure of claim 13, wherein the random copolymer is heterophasic.

16. The polymeric layer structure of claim 8, wherein the propylene copolymer is obtained using a single site catalyst.

17. The polymeric layer structure of claim 1, wherein the second sealant layer is a high melt strength polypropylene.

18. The polymeric layer structure of claim 17, wherein the high melt strength polypropylene is selected from the group of: polypropylene homopolymers and polypropylene copolymers.

19. The polymer layer structure of claim 1, wherein the second sealant layer is a blend of polypropylene and α-olefin copolymers.

20. The polymeric layer structure of claim 19, wherein the number of carbon atoms in at least two polypropylene and α-olefin copolymers is different.

21. The polymeric layer structure of claim 1, wherein the seal is capable of being peeled apart by using hand pressure.

22. The polymeric layer structure of claim 1 further comprising a first external layer attached to the first sealant layer.

23. The polymeric layer structure of claim 22, wherein the first external layer is selected from the group consisting of (1) polyolefins, (2) polyamides, (3) polyesters, (4) ethylene copolymerized with one or more monomers comprising: (a) carboxylic acids having from 2 to 20 carbons and (b) ester derivatives thereof, (c) acrylic acid, (d) ester derivatives or acrylic acids, (e) alkyl substituted acrylic acid, (f) alkyl substitutes esters of acrylic acid, (g) vinyl acetate, and (h) vinyl acrylate.

24. The polymeric layer structure of claim 23, wherein the first external layer is a polyamide.

25. The polymeric layer structure of claim 24, wherein the polyamide is nylon 6.

26. The polymeric layer structure of claim 22 further comprising a second external layer attached to the second sealant layer.

27. The polymeric layer structure of claim 26 where the second external layer is selected from the group consisting of (1) polyolefins, (2) polyamides, (3) polyesters, (4) ethylene copolymerized with one or more monomers comprising: (a) carboxylic acids having from 2 to 20 carbons and (b) ester derivatives thereof, (c) acrylic acid, (d) ester derivatives or acrylic acids, (e) alkyl substituted acrylic acid, (f) alkyl substitutes esters of acrylic acid, (g) vinyl acetate, and (h) vinyl acrylate.

28. The polymeric layer structure of claim 27, wherein the second external layer is a polyamide.

29. The polymeric layer structure of claim 28, wherein the polyamide is nylon 6.

30. The polymeric layer structure of claim 1, wherein the seal has a strength of about 0.5 N to about 7.6 N when pulling forces are applied to the seal in a direction parallel to the direction of the seal.

31. The polymeric layer structure of claim 30, wherein the seal strength does not vary by more than approximately 50% when comparing the structure being subjected to a steam autoclave process and after being subjected to a steam autoclave process at 121° C. for one hour.

32. The polymeric layer structure of claim 27, wherein the second external layer is a polyolefin.

33. The polymeric layer structure of claim 32, wherein the polyolefin is linear low density polyethylene.

34. An overpouch container comprising:
a first sidewall having a first sealant layer composed solely of an ethylene homopolymer; and
a second sidewall having a second sealant layer of a propylene containing polymer, the second sealant layer being attached to the first sealant layer along a peelable peripheral seal.

35. The overpouch of claim 34, wherein the ethylene homopolymer is selected from the group consisting of high density polyethylene, medium density polyethylene and linear low density polyethylene.

36. The overpouch of claim 35, wherein the first sealant layer is high density polyethylene.

37. The overpouch of claim 34, wherein the second sealant layer is selected from the group consisting of: propylene homopolymers and propylene copolymers.

38. The overpouch of claim 37, wherein the second sealant layer is a propylene homopolymer.

39. The overpouch of claim 38, wherein the propylene homopolymer has a stereochemistry selected from the group of: (a) amorphous, (b) isotactic, (c) syndiotactic, (d) atactic, (e) hemiisotactic, and (f) stereoblock.

40. The overpouch of claim 38, wherein the propylene homopolymer is obtained using a single site catalyst.

41. The overpouch of claim 37, wherein the second sealant layer is a propylene copolymer.

42. The overpouch of claim 41, wherein the propylene copolymer is obtained by polymerizing a propylene monomer with an α-olefin having from 2 to 20 carbons.

43. The overpouch of claim 41, wherein propylene is copolymerized with ethylene in an amount by weight from about 1% to about 20% of the copolymer.

44. The overpouch of claim 43, wherein propylene is copolymerized with ethylene in an amount by weight from about 1% to about 10% of the copolymer.

45. The overpouch of claim 43, wherein propylene is copolymerized with ethylene in an amount by weight from about 2% to about 5% of the copolymer.

46. The overpouch of claim 43, wherein the propylene and ethylene copolymer is a random copolymer.

47. The overpouch of claim 43, wherein the propylene and ethylene copolymer is a block copolymer.

48. The overpouch of claim 46, wherein the random copolymer is heterophasic.

49. The overpouch of claim 41, wherein the propylene copolymer is obtained using a single site catalyst.

50. The overpouch of claim 34, wherein the second sealant layer is a high melt strength polypropylene.

51. The overpouch of claim 50, wherein the high melt strength polypropylene is selected from the group of: polypropylene homopolymers and polypropylene copolymers.

52. The overpouch of claim 34, wherein the second sealant layer is a blend of polypropylene and α-olefin copolymers.

53. The overpouch of claim 52, wherein the number of carbon atoms in at least two polypropylene and α-olefin copolymers is different.

54. The overpouch of claim 34, wherein the seal is capable of being peeled apart by using hand pressure.

55. The overpouch of claim 34, further comprising a first external layer attached to the first sealant layer.

56. The overpouch of claim 55, wherein the first external layer is selected from the group consisting of (1) polyolefins, (2) polyamides, (3) polyesters, (4) ethylene copolymerized with one or more monomers comprising: (a) carboxylic acids having from 2 to 20 carbons and (b) ester derivatives thereof, (c) acrylic acid, (d) ester derivatives or acrylic acids, (e) alkyl substituted acrylic acid, (f) alkyl substitutes esters of acrylic acid, (g) vinyl acetate, and (h) vinyl acrylate.

57. The overpouch of claim 56, wherein the first external layer is a polyamide.

58. The overpouch of claim 57, wherein the polyamide is nylon 6.

59. The overpouch of claim 55, further comprising a second external layer attached to the second sealant layer.

60. The overpouch of claim 59, where the second external layer is selected from the group consisting of (1) polyolefins, (2) polyamides, (3) polyesters, (4) ethylene copolymerized with one or more monomers comprising: (a) carboxylic acids having from 2 to 20 carbons and (b) ester derivatives thereof, (c) acrylic acid, (d) ester derivatives or acrylic acids, (e) alkyl substituted acrylic acid, (f) alkyl substitutes esters of acrylic acid, (g) vinyl acetate, and (h) vinyl acrylate.

61. The overpouch of claim 60, wherein the second external layer is a polyamide.

62. The overpouch of claim 61, wherein the polyamide is nylon 6.

63. The overpouch of claim 34, wherein the seal has a strength of about 0.5 N to about 7.6 N when pulling forces are applied to the seal in a direction parallel to the direction of the seal.

64. The overpouch of claim 63, wherein the seal strength does not vary by more than approximately 50% when comparing the structure being autoclaved and after being subjected to a steam autoclave process at 121° C. for one hour.

65. The overpouch of claim 60, wherein the second external layer is a polyolefin.

66. The overpouch of claim 65, wherein the polyolefin is linear low density polyethylene.

* * * * *